(12) United States Patent
Vanney et al.

(10) Patent No.: US 7,419,489 B2
(45) Date of Patent: *Sep. 2, 2008

(54) ABLATION CATHETER ASSEMBLY HAVING A VIRTUAL ELECTRODE COMPRISING PORTHOLES

(75) Inventors: Guy P. Vanney, Blaine, MN (US); Jeremy D. Dando, Plymouth, MN (US); Joshua L. Dudney, Minneapolis, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/328,565

(22) Filed: Jan. 10, 2006

(65) Prior Publication Data

US 2006/0111708 A1    May 25, 2006

Related U.S. Application Data

(62) Division of application No. 10/347,034, filed on Jan. 17, 2003, now Pat. No. 6,984,232.

(51) Int. Cl.
*A61B 18/14* (2006.01)
(52) U.S. Cl. .................. 606/41; 606/49; 607/105; 607/113
(58) Field of Classification Search ............ 606/27–29, 606/31–32, 41, 42, 49; 607/96, 98, 1, 104, 607/105, 113
See application file for complete search history.

(56) References Cited

U.S. PATENT DOCUMENTS

| | | |
|---|---|---|
| 4,945,912 A | 8/1990 | Langberg |
| 5,281,213 A | 1/1994 | Milder et al. ............ 606/15 |
| 5,281,217 A | 1/1994 | Edwards et al. ............ 606/41 |

(Continued)

FOREIGN PATENT DOCUMENTS

WO        99/48421 A        9/1999

OTHER PUBLICATIONS

Office action mailed Jun. 8, 2007 in related U.S. Appl. No. 10/608,257.

(Continued)

*Primary Examiner*—Lee S Cohen
(74) *Attorney, Agent, or Firm*—Wiley & Rein LLP

(57) ABSTRACT

An ablation catheter having a catheter shaft and a virtual electrode, the virtual electrode comprising portholes through an outer peripheral wall of the catheter shaft and a metal electrode, the catheter being used for treatment of cardiac arrhythmia, for example, atrial fibrillation, by electrically isolating a vessel, such as a pulmonary vein, from a chamber, such as the left atrium. The catheter shaft includes a proximal portion and a distal portion. The distal portion includes an active region, which is either a looped structure transverse to the longitudinal axis of the catheter shaft, or a linear structure that extends parallel to the longitudinal axis of the catheter shaft. During use, the active region is directed into contact with, for example, the wall of a pulmonary vein. Upon energization, the virtual electrode creates a continuous lesion on an inner wall of the pulmonary vein, thereby electrically isolating the pulmonary vein from the left atrium.

14 Claims, 10 Drawing Sheets

U.S. PATENT DOCUMENTS

| | | | |
|---|---|---|---|
| 5,334,193 A | 8/1994 | Nardella | 606/41 |
| 5,348,554 A | 9/1994 | Imran et al. | |
| 5,370,644 A | 12/1994 | Langberg | |
| 5,391,147 A | 2/1995 | Imran et al. | |
| 5,405,376 A | 4/1995 | Mulier et al. | |
| 5,423,811 A | 6/1995 | Imran et al. | |
| 5,431,168 A | 7/1995 | Webster, Jr. | |
| 5,431,649 A | 7/1995 | Mulier et al. | 606/41 |
| 5,433,708 A | 7/1995 | Nichols et al. | 604/113 |
| 5,478,330 A | 12/1995 | Imran et al. | |
| 5,487,757 A | 1/1996 | Truckai et al. | |
| 5,542,928 A | 8/1996 | Evans et al. | 604/113 |
| 5,545,161 A | 8/1996 | Imran | |
| 5,545,200 A | 8/1996 | West et al. | |
| 5,571,088 A | 11/1996 | Lennox et al. | |
| 5,575,766 A | 11/1996 | Swartz et al. | |
| 5,575,772 A | 11/1996 | Lennox | |
| 5,584,872 A | 12/1996 | LaFontaine et al. | 607/116 |
| 5,588,964 A | 12/1996 | Imran et al. | |
| 5,609,151 A | 3/1997 | Mulier et al. | 128/642 |
| 5,643,231 A | 7/1997 | Lurie et al. | |
| 5,656,029 A | 8/1997 | Imran et al. | |
| 5,658,278 A | 8/1997 | Imran et al. | 606/41 |
| 5,676,693 A | 10/1997 | LaFontaine | 607/116 |
| 5,680,860 A | 10/1997 | Imran | |
| 5,697,927 A | 12/1997 | Imran et al. | 606/41 |
| 5,725,524 A | 3/1998 | Mulier et al. | 606/41 |
| 5,785,706 A | 7/1998 | Bednarek | 606/41 |
| 5,792,140 A | 8/1998 | Tu et al. | |
| 5,800,482 A | 9/1998 | Pomeranz et al. | |
| 5,807,395 A | 9/1998 | Mulier et al. | |
| 5,826,576 A | 10/1998 | West et al. | |
| 5,842,984 A | 12/1998 | Avitall | |
| 5,843,152 A | 12/1998 | Tu et al. | |
| 5,846,223 A | 12/1998 | Swartz et al. | |
| 5,860,974 A | 1/1999 | Abele | |
| 5,876,398 A | 3/1999 | Mulier et al. | 606/41 |
| 5,876,399 A | 3/1999 | Chia et al. | |
| 5,882,346 A | 3/1999 | Pomeranz et al. | |
| 5,893,884 A | 4/1999 | Tu | |
| 5,895,417 A | 4/1999 | Pomeranz et al. | 607/101 |
| 5,906,605 A | 5/1999 | Coxum | |
| 5,906,613 A | 5/1999 | Mulier et al. | |
| 5,910,129 A | 6/1999 | Koblish et al. | |
| 5,913,854 A | 6/1999 | Maguire et al. | 606/41 |
| 5,913,856 A | 6/1999 | Chia et al. | 606/41 |
| 5,916,213 A | 6/1999 | Haissaguerre et al. | |
| 5,919,188 A | 7/1999 | Shearon et al. | 606/41 |
| 5,921,924 A | 7/1999 | Avitall | |
| 5,938,659 A | 8/1999 | Tu et al. | |
| 5,938,660 A | 8/1999 | Swartz et al. | |
| 5,938,694 A | 8/1999 | Jaraczewski et al. | |
| 5,971,968 A | 10/1999 | Tu et al. | 604/264 |
| 5,980,516 A | 11/1999 | Mulier et al. | |
| 5,993,462 A | 11/1999 | Pomeranz et al. | |
| 5,997,526 A * | 12/1999 | Giba et al. | 604/531 |
| 5,997,532 A | 12/1999 | McLaughlin et al. | 606/41 |
| 6,001,085 A | 12/1999 | Lurie et al. | |
| 6,004,269 A | 12/1999 | Crowley et al. | |
| 6,010,500 A | 1/2000 | Sherman et al. | 606/41 |
| 6,012,457 A | 1/2000 | Lesh | |
| 6,015,407 A | 1/2000 | Rieb et al. | 606/41 |
| 6,016,809 A | 1/2000 | Mulier et al. | 128/898 |
| 6,023,638 A | 2/2000 | Swanson et al. | |
| 6,024,740 A | 2/2000 | Lesh et al. | |
| 6,032,077 A | 2/2000 | Pomeranz | 607/101 |
| 6,048,329 A | 4/2000 | Thompson et al. | |
| 6,063,080 A | 5/2000 | Nelson et al. | 606/41 |
| 6,068,629 A | 5/2000 | Haissaguerre et al. | |
| 6,068,653 A | 5/2000 | LaFontaine | 607/116 |
| 6,071,274 A | 6/2000 | Thompson et al. | |
| 6,071,279 A | 6/2000 | Whayne et al. | |
| 6,076,012 A | 6/2000 | Swanson et al. | |
| 6,080,151 A | 6/2000 | Swartz et al. | 606/45 |
| 6,117,101 A | 9/2000 | Diederich et al. | |
| 6,119,041 A | 9/2000 | Pomeranz et al. | 607/101 |
| 6,120,476 A | 9/2000 | Fung et al. | 604/95 |
| 6,120,500 A | 9/2000 | Bednarek et al. | 606/41 |
| 6,132,426 A | 10/2000 | Kroll | 606/41 |
| 6,138,043 A | 10/2000 | Avitall | |
| 6,164,283 A | 12/2000 | Lesh | |
| 6,168,594 B1 | 1/2001 | LaFontaine et al. | 606/41 |
| 6,169,916 B1 | 1/2001 | West | |
| 6,171,275 B1 | 1/2001 | Webster, Jr. | 604/20 |
| 6,171,277 B1 | 1/2001 | Ponzi | |
| 6,183,463 B1 | 2/2001 | Webster, Jr. | |
| 6,203,525 B1 | 3/2001 | Whayne et al. | |
| 6,210,406 B1 | 4/2001 | Webster | |
| 6,212,426 B1 | 4/2001 | Swanson | |
| 6,217,573 B1 | 4/2001 | Webster | |
| 6,217,574 B1 | 4/2001 | Webster | |
| 6,217,576 B1 | 4/2001 | Tu et al. | 606/41 |
| 6,219,582 B1 | 4/2001 | Hofstad et al. | 607/122 |
| 6,231,585 B1 | 5/2001 | Takahashi et al. | |
| 6,235,021 B1 | 5/2001 | Sieben | |
| 6,235,022 B1 | 5/2001 | Hallock et al. | 606/41 |
| 6,235,025 B1 | 5/2001 | Swartz et al. | |
| 6,235,044 B1 | 5/2001 | Root et al. | 606/200 |
| 6,238,393 B1 | 5/2001 | Mulier et al. | 606/41 |
| 6,241,722 B1 | 6/2001 | Dobak et al. | 606/23 |
| 6,241,727 B1 | 6/2001 | Tu et al. | |
| 6,241,754 B1 | 6/2001 | Swanson et al. | |
| 6,245,064 B1 | 6/2001 | Lesh et al. | |
| 6,251,109 B1 | 6/2001 | Hassett et al. | |
| 6,254,599 B1 | 7/2001 | Lesh et al. | |
| 6,264,654 B1 | 7/2001 | Swartz et al. | |
| 6,290,697 B1 | 9/2001 | Tu et al. | |
| 6,305,378 B1 | 10/2001 | Lesh | |
| 6,308,091 B1 | 10/2001 | Avitall | |
| 6,325,797 B1 | 12/2001 | Stewart et al. | |
| 6,330,473 B1 | 12/2001 | Swanson et al. | |
| 6,371,955 B1 | 4/2002 | Fulmaono et al. | |
| 6,383,151 B1 | 5/2002 | Diederich et al. | |
| 6,402,476 B1 | 6/2002 | Whayne et al. | |
| 6,409,722 B1 | 6/2002 | Hoey et al. | 606/34 |
| 6,416,511 B1 | 7/2002 | Lesh et al. | |
| 6,447,506 B1 * | 9/2002 | Swanson et al. | 606/41 |
| 6,447,507 B1 * | 9/2002 | Bednarek et al. | 606/41 |
| 6,454,758 B1 | 9/2002 | Thompson et al. | |
| 6,454,766 B1 | 9/2002 | Swanson et al. | 606/41 |
| 6,503,247 B2 | 1/2003 | Swartz et al. | |
| 6,522,930 B1 | 2/2003 | Schaer et al. | |
| 6,540,744 B2 | 4/2003 | Hassett et al. | |
| 6,540,755 B2 | 4/2003 | Ockuly et al. | |
| 6,605,087 B2 | 8/2003 | Swartz et al. | 606/41 |
| 6,620,155 B2 | 9/2003 | Underwood et al. | |
| 6,702,811 B2 | 3/2004 | Stewart et al. | |
| 6,858,026 B2 | 2/2005 | Sliwa et al. | 606/28 |
| 6,960,207 B2 | 11/2005 | Vanney et al. | |
| 6,984,232 B2 * | 1/2006 | Vanney et al. | 606/41 |
| 2002/0072741 A1 | 6/2002 | Sliwa et al. | |
| 2002/0082556 A1 | 6/2002 | Cioanta et al. | |
| 2003/0130713 A1 | 7/2003 | Stewart et al. | |
| 2004/0181189 A1 | 9/2004 | Roychowdhury et al. | |
| 2005/0055019 A1 | 3/2005 | Skarda | |

OTHER PUBLICATIONS

Amendment and Response filed Oct. 9, 2007 in related U.S. Appl. No. 10/608,257.

Supplementary European Search Report for EP04703670 dated Oct. 9, 2007.

* cited by examiner

ABLATION CATHETER ASSEMBLY HAVING A VIRTUAL ELECTRODE COMPRISING PORTHOLES

CROSS-REFERENCE TO RELATED APPLICATIONS

This application is a division of U.S. utility patent application Ser. No. 10/347,034, filed 17 Jan. 2003 (the '034 application), now U.S. Pat. No. 6,984,232 B2, issued 10 Jan. 2006 (the '232 patent). The '034 application and the '232 patent are both hereby incorporated by reference as though fully set forth herein. This application is related to U.S. utility patent application Ser. No. 11/264,649, filed 1 Nov. 2005 (the '649 application), which is a division of U.S. utility patent application Ser. No. 10/608,297, filed 28 Jun. 2003 (the '297 application), now U.S. Pat. No. 6,960,207, issued 1 Nov. 2005 (the '207 patent), which claims the benefit of U.S. provisional patent application No. 60/441,849, filed 21 Jan. 2003 (the '849 application).

BACKGROUND OF THE INVENTION a. Field of the Invention

This invention relates to catheters for the mapping and ablation of human tissue, particularly cardiac tissue. In particular, the invention relates to an ablation catheter comprising a virtual electrode at a distal portion of the catheter to ablate tissue, the virtual electrode using energy emanating from a metal electrode contained within the distal portion and conductive fluid medium contacted by the metal electrode before exiting from the distal portion through a plurality of portholes.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel near the surface of the body and is guided to a specific location within the body for examination, diagnosis, and treatment. For example, one procedure utilizes a catheter to convey an electrical stimulus to a selected location within the human body. Another procedure utilizes a catheter with sensing electrodes to monitor various forms of electrical activity in the human body.

Catheters are also used increasingly for medical procedures involving the human heart. Typically, the catheter is inserted in an artery or vein in the leg, neck, or arm of the patient and threaded, sometimes with the aid of a guide wire or introducer, through the vessels until a distal tip of the catheter reaches the desired location for the medical procedure in the heart.

A typical human heart includes a right ventricle, a right atrium, a left ventricle, and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle.

In the normal heart, contraction and relaxation of the heart muscle (myocardium) takes place in an organized fashion as electro-chemical signals pass sequentially through the myocardium from the sinoatrial (SA) node, which comprises a bundle of unique cells disposed in the wall of the right atrium, to the atrioventricular (AV) node and then along a well-defined route, which includes the His-Purkinje system, into the left and right ventricles. The AV node lies near the ostium of the coronary sinus in the interatrial septum in the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole, wherein the atria contract to empty and fill blood into the ventricles. The atrial depolarization from the SA node is detected by the atrioventricular (AV) node which, in turn, communicates the depolarization impulse into the ventricles via the bundle of His and Purkinje fibers following a brief conduction delay. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart, which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Other abnormal arrhythmias sometimes occur in the atria, which are referred to as atrial arrhythmia. Three of the most common atrial arrhythmia are ectopic atrial tachycardia, atrial fibrillation, and atrial flutter. Atrial fibrillation can result in significant patient discomfort and even death because of a number of associated problems, including the following: an irregular heart rate, which causes patient discomfort and anxiety; loss of synchronous atrioventricular contractions, which compromises cardiac hemodynamics, resulting in varying levels of congestive heart failure; and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems, and other difficulties.

An increasingly common medical procedure for the treatment of certain types of cardiac arrhythmia is catheter ablation. During conventional catheter ablation procedures, an energy source is placed in contact with cardiac tissue to heat the tissue and create a permanent scar or lesion that is electrically inactive or noncontractile. During one procedure, the lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). Ablation of fast or slow AV nodal pathways is disclosed in Singer, I., et al., "Catheter Ablation for Arrhythmias," Clinical Manual of Electrophysiology, pgs. 421-431 (1993). The use of electrode catheters for ablating specific locations within the heart has also been disclosed in, for example, U.S. Pat. Nos. 4,641,649, 5,228,442, 5,231,995, 5,263,493, and 5,281,217.

Another medical procedure using ablation catheters with sheaths to ablate accessory pathways associated with W-P-W utilizing both a transseptal and retrograde approach is discussed in Saul, J. P., et al., "Catheter Ablation of Accessory Atrioventricular Pathways in Young Patients: Use of long vascular sheaths, the transseptal approach and a retrograde left posterior parallel approach," Journal of the American College of Cardiology, Vol. 21, no. 3, pgs. 571-583 (1 Mar. 1993). Other catheter ablation procedures are disclosed in Swartz, J. F., "Radiofrequency Endocardial Catheter Ablation of Accessory Atrioventricular Pathway Atrial Insertion Sites," Circulation, Vol. 87, no. 2, pgs. 487-499 (February 1993).

Ablation of a specific location within the heart requires the precise placement of the ablation catheter within the heart. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy (placement of the catheter in relation to known features of the heart, which are marked by radiopaque diagnostic catheters that are placed in or at known anatomical structures, such as the coronary sinus, high right atrium, and the right ventricle).

Ablation procedures using guiding introducers to guide an ablation catheter to a particular location in the heart for treatment of atrial arrhythmia have been disclosed in, for example, U.S. Pat. Nos. 5,427,119, 5,497,774, 5,564,440, 5,575,766, 5,628,316, and 5,640,955. During these procedures, ablation lesions are produced in the heart as an element of the medical procedure.

The energy necessary to ablate cardiac tissue and create a permanent lesion can be provided from a number of different sources. Originally, direct current was utilized although laser, microwave, ultrasound, and other forms of energy have also been utilized to perform ablation procedures. Because of problems associated with the use of DC current, however, radiofrequency (RF) has become the preferred source of energy for ablation procedures. The use of RF energy for ablation has been disclosed, for example, in U.S. Pat. Nos. 4,945,912, 5,242,441, 5,246,438, 5,281,213, 5,281,218, and 5,293,868. The use of RF energy with an ablation catheter contained within a transseptal sheath for the treatment of W-P-W in the left atrium is disclosed in Swartz, J. F. et al., "Radiofrequency Endocardial Catheter Ablation of Accessory Atrioventricular Pathway Atrial Insertion Sites," Circulation, Vol. 87, pgs. 487-499 (1993). See also Tracey, C. N., "Radio Frequency Catheter Ablation of Ectopic Atrial Tachycardia Using Paced Activation Sequence Mapping," J. Am. Coll. Cardiol. Vol. 21, pgs. 910-917 (1993).

In addition to radiofrequency ablation catheters, thermal ablation catheters have been disclosed. During thermal ablation procedures, a heating element, secured to the distal end of a catheter, heats thermally conductive fluid, which fluid then contacts the human tissue to raise its temperature for a sufficient period of time to ablate the tissue. A method and device for thermal ablation using heat transfer is disclosed in U.S. Pat. No. 5,433,708. Another thermal ablation procedure utilizing a thermal electrode secured to a catheter and located within a balloon with openings in that balloon to permit heated conductive fluid introduced into the balloon from the catheter to escape from the balloon for contact with the tissue to be ablated is disclosed in U.S. Pat. No. 5,505,730.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes as disclosed in, for example, U.S. Pat. Nos. 4,892, 102, 5,228,442, 5,327,905, 5,354,297, 5,487,385, and 5,582, 609.

To form linear lesions within the heart using a conventional ablation tip electrode requires the utilization of procedures such as a "drag burn." The term "linear lesion" as used herein means and elongate, continuous lesion, whether straight or curved, that blocks electrical conduction. During a "drag burn" procedure, while ablating energy is supplied to the tip electrode, the tip electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure, and other variables associated with a beating heart, especially an erratically beating heart. Unless an uninterrupted track of cardiac tissue is ablated, unablated tissue or incompletely ablated tissue may remain electrically active, permitting the continuation of the stray circuit that causes the arrhythmia.

It has been discovered that more efficient ablation may be achieved if a linear lesion of cardiac tissue is formed during a single ablation procedure. The production of linear lesions in the heart by use of an ablation catheter is disclosed in, for example, U.S. Pat. Nos. 5,487,385, 5,582,609, and 5,676, 662. A specific series of linear lesions formed in the atria for the treatment of atrial arrhythmia are disclosed in U.S. Pat. No. 5,575,766.

The ablation catheters commonly used to perform these ablation procedures produce electrically inactive or noncontractile tissue at a selected location by physical contact of the cardiac tissue with an electrode of the ablation catheter. Conventional tip electrodes with adjacent ring electrodes cannot perform this type of procedure, however, because of the high amount of energy that is necessary to ablate sufficient tissue to produce a complete linear lesion. Also, conventional ring electrode ablation may leave holes or gaps in a lesion, which can provide a doorway through which unwanted circuits can travel.

An ablation catheter for use in the heart that contains a pair of intertwined helical electrodes is disclosed in U.S. Pat. No. 5,334,193. The helically wound electrode is affixed to the surface of the catheter body over a distance of about eight centimeters from the distal tip of the catheter body. Other helical electrodes are disclosed in U.S. Pat. Nos. 4,161,952, 4,776,334, 4,860,769, 4,934,049, 5,047,026, 5,542,928, and WO 95/10319.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode, which often results in the formation of coagulum on the electrode, which reduces the efficiency of the ablation electrode.

To achieve efficient and effective ablation, coagulation of blood that is common with conventional ablation catheters should be avoided. This coagulation problem can be especially significant when linear ablation lesions or tracks are produced because such linear ablation procedures conventionally take more time than ablation procedures ablating only a single location.

In some instances, stray electrical signals find a pathway down the pulmonary veins and into the left atrium of the heart. In these instances, it may be advantageous to produce a circumferential lesion at the ostium of one or more of the pulmonary veins or within one or more of the pulmonary veins. Desirably, such a circumferential lesion would electrically isolate a pulmonary vein from the left atrium, completely blocking stray signals from traveling down the pulmonary vein and into the left atrium. It is desirable to have a catheter tip for forming such circumferential lesions in tissue while avoiding problems with existing designs.

BRIEF SUMMARY OF THE INVENTION

It is an object of the disclosed invention to provide an improved ablation catheter for forming linear lesions in tissue, including tissue within the human heart and the pulmonary veins. This and other objects are provided by the ablation catheter that is disclosed by the present invention.

The instant invention is a catheter for ablating tissue and, in one form, comprises a catheter shaft and a metal electrode. The metal electrode may be a platinum flat wire adapted to be connected to an RF generator. The catheter shaft has a proximal portion, a distal portion, and at least one lumen that extends from the proximal portion to the distal portion. The distal portion is adapted to be inserted into a body cavity having tissue to be ablated and may be straight or curved. The distal portion comprises an active region that includes a plurality of portholes. The first lumen is adapted to carry a conductive fluid medium from the proximal portion to the portholes along the active region of the distal portion. In one form of the invention, each of the portholes is sized so that the conductive fluid medium flows evenly from each of the portholes. The metal electrode, which is adapted to supply ablation energy to the conductive fluid medium, is mounted in the first lumen and extends along the active region of the distal portion.

In another form of the ablation catheter of the instant invention, the catheter comprises a catheter shaft, a metal electrode, and a shape memory wire. The catheter shaft has a proximal portion, a distal portion, a first lumen that extends from the proximal portion to the distal portion, and a second lumen. The distal portion comprises at least one curved portion that is configured to be inserted into a body cavity having tissue to be ablated. For example, the at least one curved portion may comprise a circular section designed to fit within a pulmonary vein around a longitudinal axis of the pulmonary vein. The at least one curved portion defines an inner peripheral wall and an outer peripheral wall, wherein the outer peripheral wall has an active region that includes a plurality of portholes. The first lumen is adapted to carry a conductive fluid medium from the proximal portion to the portholes along the active region of the distal portion. The metal electrode, which is adapted to supply ablation energy to the conductive fluid medium, is mounted in the first lumen and extends along the active region of the distal portion. The second lumen extends adjacent to the inner peripheral wall. The shape memory wire is mounted in the second lumen. The shape memory wire may comprise, for example, an alloy of nickel and titanium (e.g., NiTi) or a strip of stainless steel.

In still another form of the present invention, the portholes along the active region of the distal portion comprise a first porthole, at least one intermediate porthole, and a last porthole. The portholes are circular in cross section, and the relative diameter of the portholes increases in size as one moves distally along the active region, from the first porthole to the last porthole. A bridge is defined between adjacent portholes. Each bridge spans a gap between a proximal leading edge of one porthole and a distal trailing edge of a next adjacent porthole. The relative width of the bridges may decrease in size as one moves distally along the active region from the first porthole to the last porthole.

In another form, the ablation catheter described above is combined with at least one guiding introducer (e.g., an inner guiding introducer and an outer guiding introducer) or a pre-curved sheath, and at least one hemostasis valve to form a complete ablation catheter assembly for treatment of cardiac arrhythmia The present invention also includes a method for making a catheter assembly for treating cardiac arrhythmia. In one form, the method comprises the steps of acquiring a shape memory wire having a desired curvilinear shape; acquiring a catheter shaft having a first lumen formed therein; inserting the shape memory wire into the first lumen to form a catheter assembly; heating the catheter shaft until it relaxes and at least partially conforms to the shape of the shape memory wire; and cooling the catheter assembly. The heating step requires heating the catheter assembly to a temperature that permits the catheter shaft to deform, but ensuring that the temperature remains lower than the temperature used to fix the shape of the shape memory wire.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 5 is a fragmentary view of the distal portion of the ablation catheter depicted in FIGS. 1-4, looking perpendicular to the longitudinal axis of the catheter shaft and perpendicular to the direction from which FIG. 4 is taken.

DETAILED DESCRIPTION OF THE INVENTION

Figure 1:
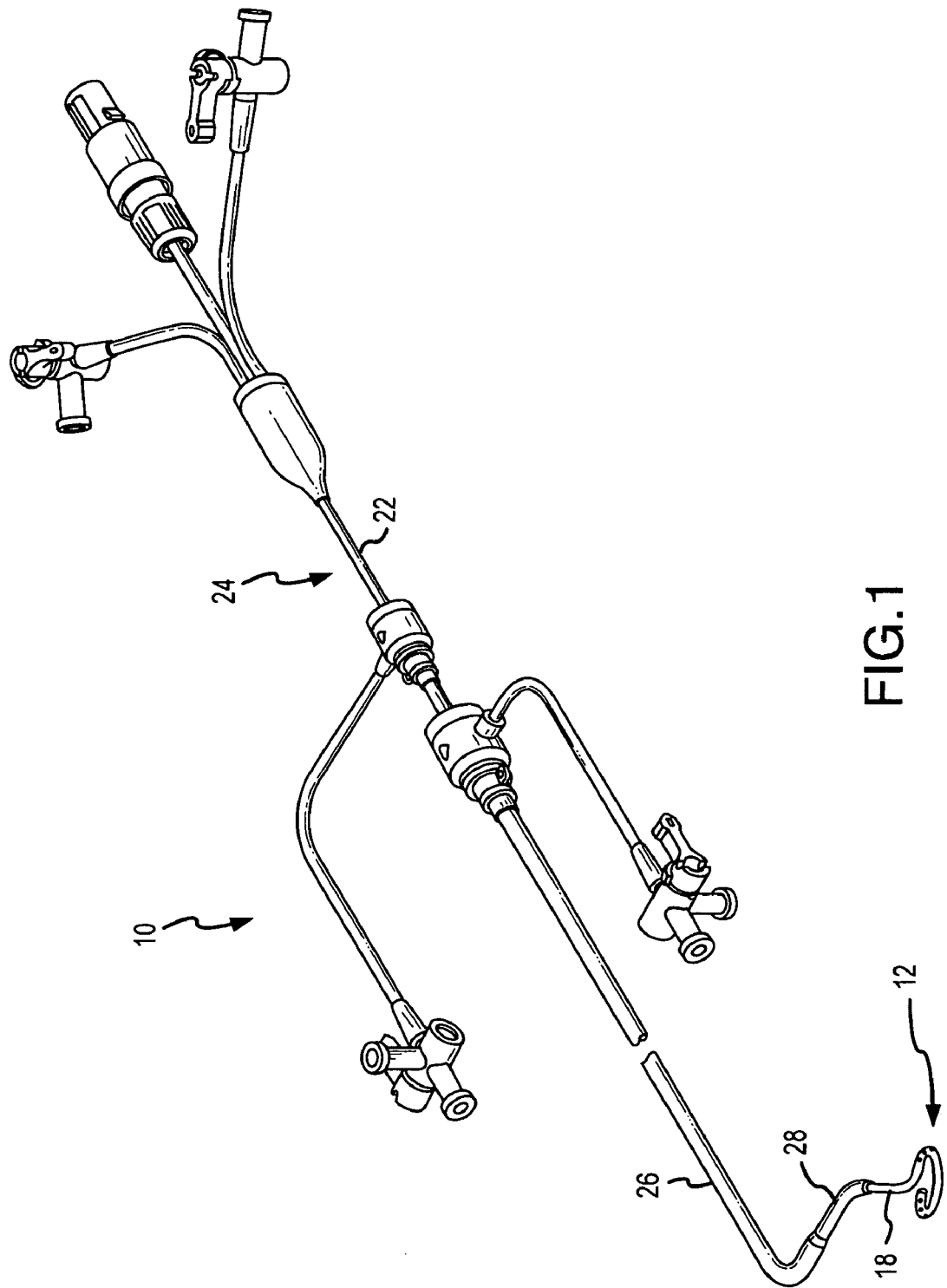
FIG. 1 is an isometric view of an ablation catheter assembly according to the present invention.

In general, the instant invention relates to an ablation catheter assembly 10 comprising an ablation catheter 18 having a unique distal portion 12 for ablating tissue 14 using energy emanating from an electrode 16 contained within the ablation catheter 18. A conductive fluid medium 20 (e.g., hypertonic saline) contacting the electrode 16 and the tissue 14 to be ablated comprises a virtual electrode, eliminating the need for direct contact between the electrode 16 and the tissue 14 to be ablated.

FIG. 1 is an isometric view looking downwardly at an ablation catheter assembly 10 according to the present invention. In this embodiment of the catheter assembly 10, an ablation catheter 18 comprising a catheter shaft 22 having a proximal portion 24 and a distal portion 12 is used in combination with one or more guiding introducers 26, 28 to facilitate formation of lesions on tissue 14, for example, cardiovascular tissue. The catheter shaft 22 may be constructed from a number of different polymers (e.g., PELLETHANE, polypropylene, oriented polypropylene, polyethylene, crystallized polyethylene terephthalate, polyethylene terephthalate, polyester, polyvinyl chloride, etc.). As depicted in FIG. 1, the ablation catheter 18 may be used in combination with an inner guiding introducer 28 and an outer guiding introducer 26. Alternatively, a single guiding introducer may be used or a precurved transseptal sheath may be used instead of one or more guiding introducers. In general, the introducer, introducers, or precurved sheath are shaped to facilitate placement of the ablation catheter 18 at the tissue 14 to be ablated. Thus, for example, the introducer or the introducers or the transseptal sheath make it possible to navigate to the heart 30 and through its complex physiology to reach specific tissue 14 to be ablated. When the ablation catheter 18 has a specific configuration like the curved configuration depicted in FIGS. 1-5, the shape of the introducers 26, 28, if used, may change somewhat when the distal portion 12 of the ablation catheter 18 is retracted into the introducers 26, 28. This effect is accounted for by the present design.

Referring more particularly to FIGS. 2-5, further details concerning the first embodiment of the ablation catheter 18 according to the present invention are described next. The distal portion 12 of the catheter shaft 22 includes a first curved section 34 of catheter shaft, a second curved section 36 of catheter shaft, and a third curved section 38 of catheter shaft, which together comprise a single unitary component in this embodiment, but which could comprise separate pieces that have been joined together. In this embodiment, the third curved section defines an active region used to ablate tissue. The catheter shaft 22, which is typically a braided shaft, includes a "straight" section 32 that may follow a circuitous path from the location of the distal portion 12 of the catheter shaft 22 adjacent to the tissue 14 to be ablated back to the proximal portion 24 of the catheter shaft 22, which is outside of the body containing the tissue 14 to be ablated. The straight section 32 is joined to the distal portion 12 by an RF bond. The third curved section 38 of catheter shaft includes a plurality of portholes through which conductive fluid medium 20 flows while the ablation catheter 18 is in use.

The plurality of portholes depicted in FIGS. 2-5 includes an initial or first porthole 40, a plurality of intermediate portholes 42, and a final or last porthole 44, which are described in more detail below. This third curved section 38 of catheter shaft is shaped in a circular, nearly closed "C" configuration, as most clearly shown in FIG. 3. The first and second curved sections 34, 36, respectively, tie the straight section 32 to the third section 38 of catheter shaft, while placing the straight section 32 of catheter shaft in a position where a longitudinal axis 46 (see FIGS. 2 and 3) extending through the straight section 32 of catheter shaft as depicted in the figures would pass through roughly the center of the open circle formed by the third curved section 38 of catheter shaft. With the straight section 32 of catheter shaft approximately equally displaced from the outer peripheral wall 48 of the third section 38 of catheter shaft, the straight section 32 of catheter shaft is less likely to press against the wall of, for example, a pulmonary vein that is being ablated during use of the ablation catheter 18. This may be seen in, for example, FIG. 12, which depicts the ablation catheter 18 in the left superior pulmonary vein 50 with the straight section 32 of catheter shaft extending along the longitudinal axis of the left superior pulmonary vein 50. Other curved sections could be used in place of the first curved section 34 of catheter shaft and the second curved section 36 of catheter shaft if it were desired to place the straight section 32 of catheter shaft in a different position relative to the third section 38 of catheter shaft, which contains the portholes that facilitate the formation of lesions.

As shown to good advantage in FIGS. 2-5, the portholes 40-44 formed in the radial apex of the outer peripheral wall 48 of the third curved section 38 of catheter shaft are circular and increase in diameter from the initial or first porthole 40 to the final or last porthole 44. In other words, the porthole with the smallest diameter is the initial porthole 40 and the porthole with the largest diameter is the last porthole 44. Also in this embodiment, the distance 52 (see FIG. 3 and compare 52' of FIG. 6A) between the centers of adjacent portholes remains substantially constant. Thus, there is a bridge 54 between adjacent portholes, and the width of the bridges narrows as one moves from the first porthole 40 through the intermediate portholes 42 to the last porthole 44. The bridge 54 spans the gap between, for example, the distal trailing edge 56 of one porthole 40-44 and the proximal leading edge 58 of the next adjacent porthole (see FIG. 7).

Figure 6:
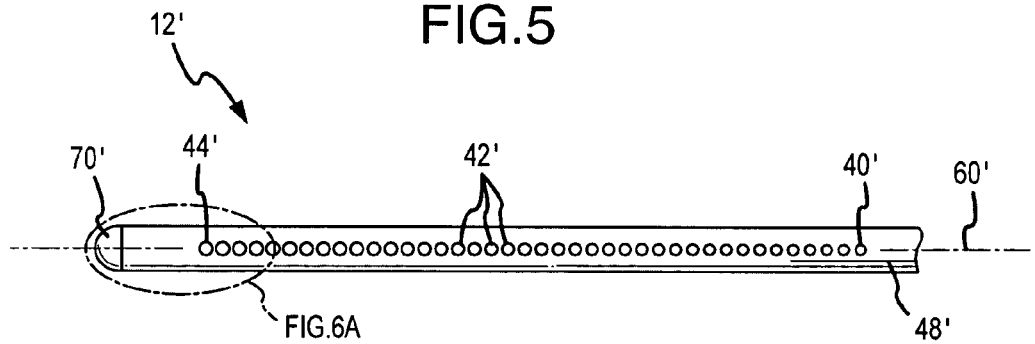
FIG. 6 is a fragmentary view of a distal portion of an ablation catheter similar to the ablation catheter depicted in FIG. 1-5, but wherein an active region of the catheter is not curved.
Figure 6A:
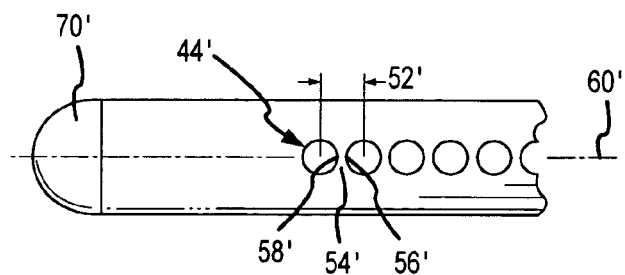
FIG. 6A is an enlarged, fragmentary view of the circled portion of FIG. 6.

In the embodiment depicted in FIGS. 6 and 6A, the distal portion 12 of the ablation catheter 18 of FIGS. 1-5 and 7 has essentially been straightened out to form a linear distal portion 12'. In other words, the complex curved configuration of the distal portion 12 depicted in FIGS. 1-5 and 7 is not present in the embodiment depicted in FIGS. 6 and 6A. The specific embodiment of a distal portion 12' depicted in FIGS. 6 and 6A does, however, similarly have an active region including a first porthole 40', intermediate portholes 42', and a last porthole 44', wherein the relative diameter of the portholes 40'-44' increases and the bridges 54' between adjacent portholes decreases or narrows in size as one moves from the first porthole 40' to the last porthole 44'. Also as clearly depicted in FIGS. 6 and 6A, the circular portholes 40'-44' are centered along a porthole centerline 60', which is a tangent line on the surface of the catheter shaft and extends parallel to the longitudinal axis of the catheter shaft on the outer peripheral wall 48' of the distal portion 12' of the ablation catheter. This is also true for the embodiment depicted in FIGS. 1-5 and 7, wherein the distal portion 12 is curved. In other words, the portholes 40-44 depicted in FIGS. 1-5 and 7 are also centered on a porthole centerline 60 (FIG. 5), which is a longitudinally extending tangent line on the radial apex of the outer peripheral wall 48 of the third curved section 38 of catheter shaft.

As alluded to above, the portholes permit a conductive fluid medium 20, which contacts a metal electrode 16 (e.g., a platinum flat wire) embedded in the ablation catheter 18, to exit the distal portion 12 of the ablation catheter 18 and contact adjacent tissue 14 to be ablated. In the embodiment depicted in FIG. 7, a metal electrode 16 is connected to an RF generator (not shown) by an electrical lead 62, which extends down the catheter shaft 22 to the proximal portion 24 of the catheter shaft 22 where it is connected to the RF generator in a known manner. In this embodiment, the metal electrode 16 emits RF energy 64 (see FIG. 13), which exits the portholes to the adjacent tissue. The embodiment depicted in FIGS. 1-5 and 7 also preferably includes a shape memory wire 66 (e.g., a flat wire comprising an alloy of nickel and titanium, known commercially as NiTi wire or Nitinol wire), which helps the distal portion 12 of the ablation catheter 18 maintain a desired configuration.

"Shape memory wire" as used herein means a strip of material (e.g., a circular or flat wire) which has the property that after deformation it will return to its former shape when heated to a certain transition temperature. Thus, "shape memory wire" is wire that has been deformed to a desired shape and briefly heated to "fix" that shape. The wire possesses a "memory" causing it to return to its fixed shape after being deformed. In the present invention, the shape memory wire 66 helps a distal portion 12 of the ablation catheter 18 take and hold a desired profile or shape. Alternatively, the shape memory wire 66 could comprise a strip of stainless steel or another resilient metal, or it could comprise a plastic material.

In the embodiment depicted in FIGS. 1-5 and 7, the portholes 40-44 are formed through the radial apex of the outer peripheral wall 48 of the third curved section 38 of catheter shaft, and the shape memory wire 66 is located within the ablation catheter 18 adjacent to the inner peripheral wall 68 of the distal portion 12. A rounded tip 70 may comprise the most distal end of the ablation catheter 18, and this tip 70 may be a tip electrode. If a tip electrode is present at the most distal end of the ablation catheter 18, it may receive energy from either the same lead 62 that is connected to the metal electrode 16, or a second lead (not shown) may be inserted along the ablation catheter to separately power the tip electrode.

Figure 7:
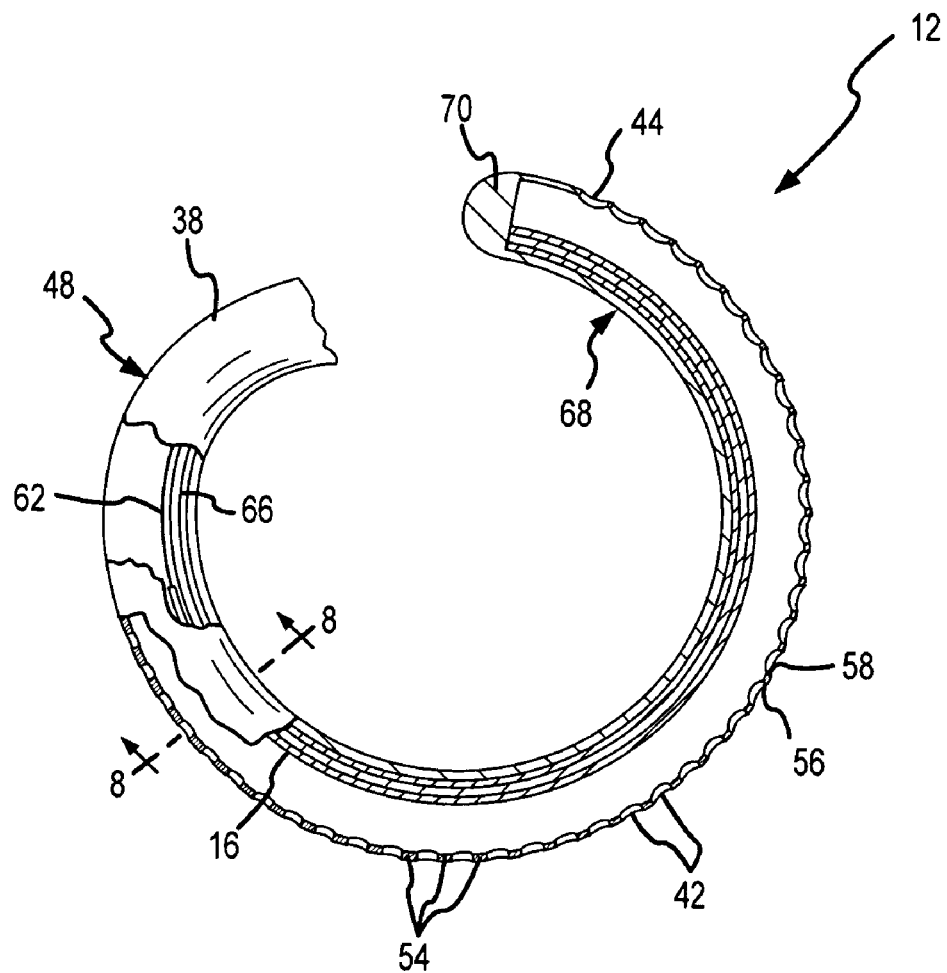
FIG. 7 is a fragmentary view taken along line 7-7 of FIG. 5, wherein portions of the ablation catheter wall have been broken away to reveal internal features of the distal portion.
Figure 8:
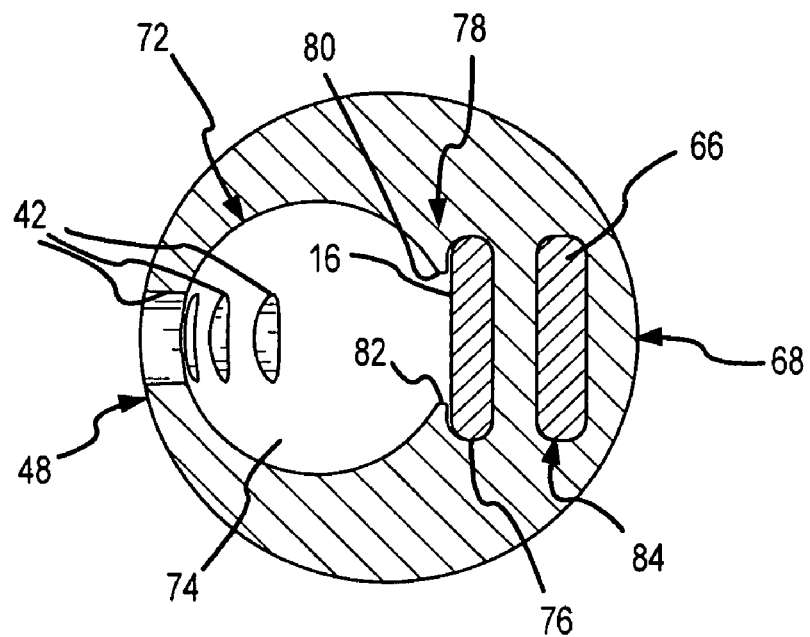
FIG. 8 is a cross-sectional view taken along line 8-8 of FIG. 7 and clearly shows an electrode in a first lumen and a shape memory wire in a second lumen.

FIG. 8 is a cross-sectional view along line 8-8 of FIG. 7 and shows further details concerning the internal configuration of the ablation catheter 18 depicted in FIG. 7. It is apparent from FIG. 8 that this variant of the ablation catheter 18 includes a bi-lumenal catheter shaft. The bi-lumenal shaft in this variant includes a first lumen 72, which has a modified keyhole shape comprising a nearly-circular subportion 74 mated with a rounded-rectangular subportion 76. These subportions 74, 76 of the first lumen 72 are joined at a necked down area 78 defining a pair of retention ledges 80, 82. In this embodiment, these retention ledges 80, 82 retain the metal electrode 16 in the rounded-rectangular subportion 76 of the first lumen 72. The nearly-circular subportion 74 of the first lumen 72 carries a conductive fluid medium 20 (see FIG. 13), which, by design, flows past, and in contact with, the metal electrode 16. A number of portholes 42 are visible in FIG. 8 through the radial apex of the outer peripheral wall 48 of the distal portion 12. A second lumen 84 depicted in cross-section in FIG. 8 carries the shape memory wire 66 (e.g., a NiTi flat wire) adjacent to the inner peripheral wall 68 of the distal portion 12. In this particular embodiment, the shape memory wire 66 does not directly contact the conductive fluid medium 20 flowing into the patient's bloodstream. Thus, it would be possible to use a shape memory wire 66 constructed from any material without regard to that material's biocompatibility.

Figure 9:
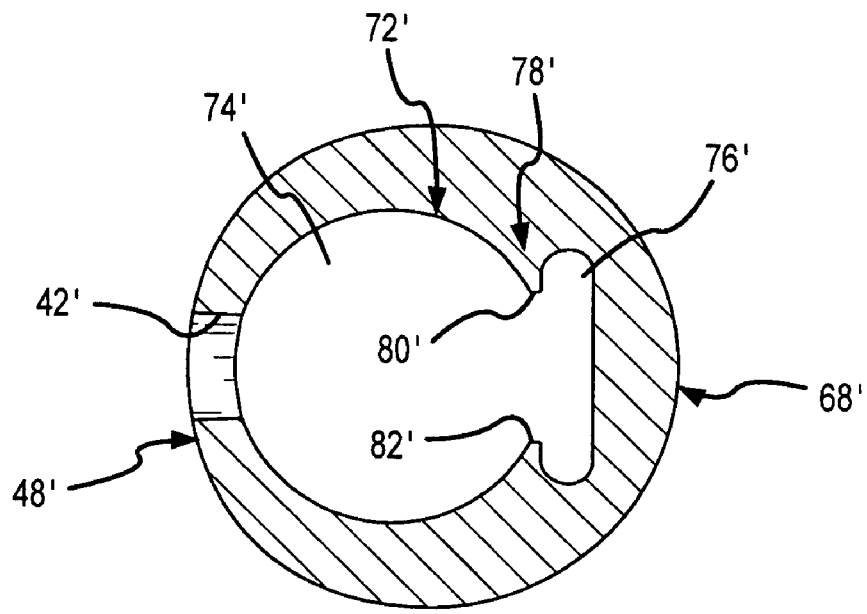
FIG. 9 depicts an alternative cross-sectional shape for the distal portion of an ablation catheter according to the present invention, wherein a single lumen is present and a separate shape memory wire is not used.

FIG. 9 depicts another possible cross-sectional configuration for the ablation catheter. In this embodiment, only a first lumen 72' is present. FIG. 9 also depicts a mere slice of the ablation catheter and, thus, only a single intermediate porthole 42' through the radial apex of the outer peripheral wall 48' is visible in FIG. 9. Similar to what is depicted in FIG. 8, the first lumen 72' depicted in FIG. 9 has a modified keyhole shape, comprising a nearly-circular subportion 74' mated with a rounded-rectangular subportion 76' adjacent to inner peripheral wall 68'. In this embodiment, a metal electrode (not shown in FIG. 9) would be retained in the rounded-rectangular subportion 76' of the first lumen 72' by retention ledges 80', 82' at necked down area 78', and would provide both the energy for the ablation procedure as well as the shape stability. For example, a NiTi flat wire could be placed in the rounded-rectangular subportion 76' of the first lumen 72' to serve as both the electrode and to provide configuration stability. If desired, the NiTi flat wire could be coated with a more conductive material (e.g., platinum, which is biocompatible with blood).

Figure 10:
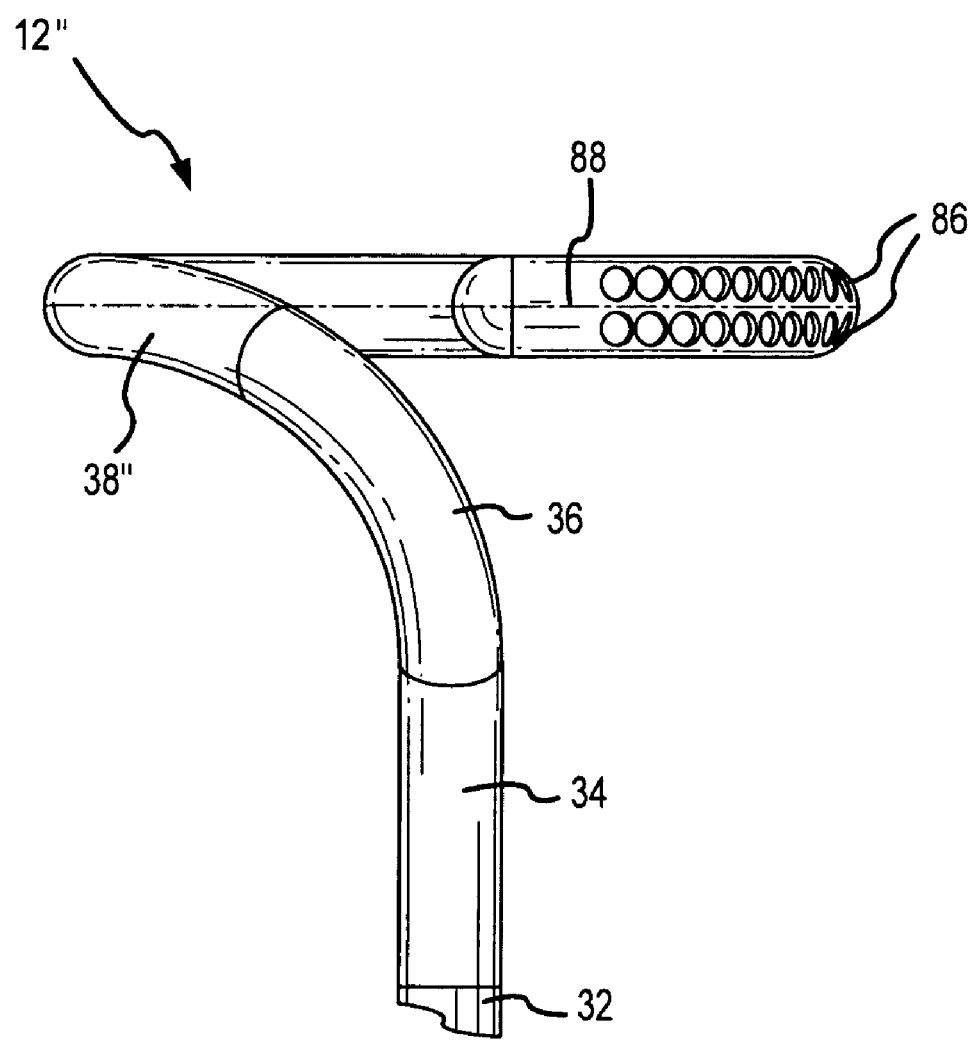
FIG. 10 is a view similar to FIG. 5, but depicts an alternate configuration for the distal portion of the ablation catheter, wherein the portholes are arranged in parallel rows.

FIG. 10 depicts an alternative embodiment for the distal portion 12" of an ablation catheter according to the present invention. This embodiment is most similar to the embodiment depicted in FIG. 5, but a third curved section 38" includes two rows 86 of portholes. In this second embodiment, each porthole has a corresponding porthole on the opposite side of the longitudinally-extending, circumferential tangent line 88 shown in this figure as bisecting the two rows 86 of portholes. The portholes could be staggered rather than side-by-side. This two row embodiment would provide a wider lesion than the lesion provided by the distal portion 12 depicted in FIG. 5, but would require a correspondingly greater amount of energy to produce a sufficient lesion in the tissue being ablated.

Figure 11:
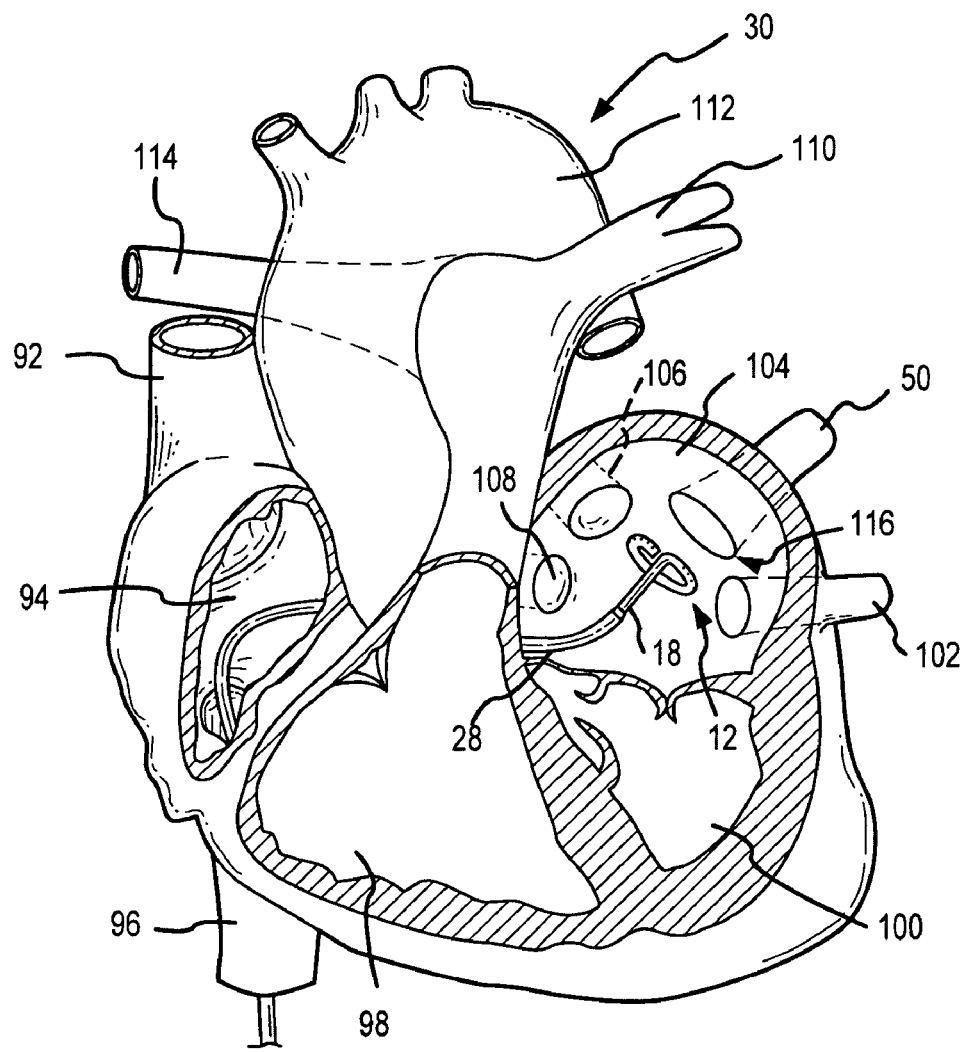
FIG. 11 is an isometric view of a heart with portions of the atria and ventricles broken away to reveal positioning of the ablation catheter depicted in, for example, FIGS. 1-5 in the left atrium prior to insertion of the ablation catheter into the left superior pulmonary vein.
Figure 12:
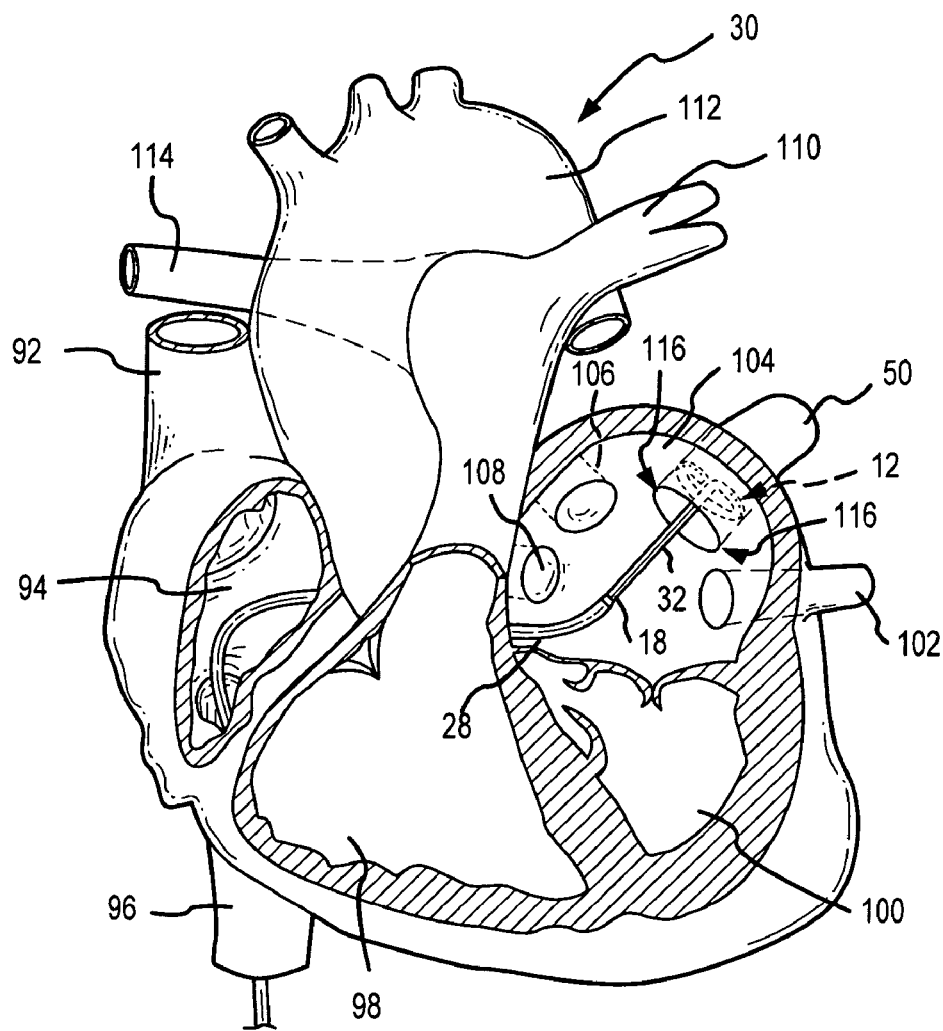
FIG. 12 is similar to FIG. 11, but depicts the ablation catheter in position within the left superior pulmonary vein.

FIGS. 11-14 depict the ablation catheter according to the present invention while being used to ablate tissue in a left superior pulmonary vein 50. FIGS. 11 and 12 include a number of primary components of the heart to orient the reader. In particular, starting in the upper left-hand portion of FIGS. 11 and 12, and working around the periphery of the heart 30 in a counterclockwise fashion, the following parts of the heart 30 are depicted: superior vena cava 92, right atrium 94, inferior vena cava 96, right ventricle 98, left ventricle 100, left inferior pulmonary vein 102, left superior pulmonary vein 50, left atrium 104, right superior pulmonary vein 106, right inferior pulmonary vein 108, left pulmonary artery 110, arch of aorta 112, and right pulmonary artery 114. The distal portion 12 of the ablation catheter 18 is positioned adjacent to the ostium 116 of the left superior pulmonary vein 50 using known procedures like the "Seldinger technique." For example, to get the distal portion 12 of the ablation catheter 18 in the position shown in FIG. 11, the right venous system may be first accessed using the "Seldinger technique," wherein a peripheral vein (such as a femoral vein) is punctured with a needle, the puncture wound is dilated with a dilator to a size sufficient to accommodate an introducer (e.g., 28). The introducer (e.g., 28) with at least one hemostasis valve (see FIG. 1) is seated within the dilated puncture wound while maintaining relative hemostasis. With the introducer in place, the ablation catheter 18 is introduced through the hemostasis valve of the introducer and is advanced along the peripheral vein, into the region of the vena cava (e.g., the inferior vena cava 96), and into the right atrium 94. From there, the ablation catheter 18 together with the guiding introducer or transseptal sheath is further advanced through a hole in the interatrial septum, which a doctor would make before inserting the ablation catheter 18 into the introducer, and into the left atrium. Once the ablation catheter 18 is in the left atrium, it can be advanced to the respective positions depicted in FIGS. 11 and 12.

Figure 13:
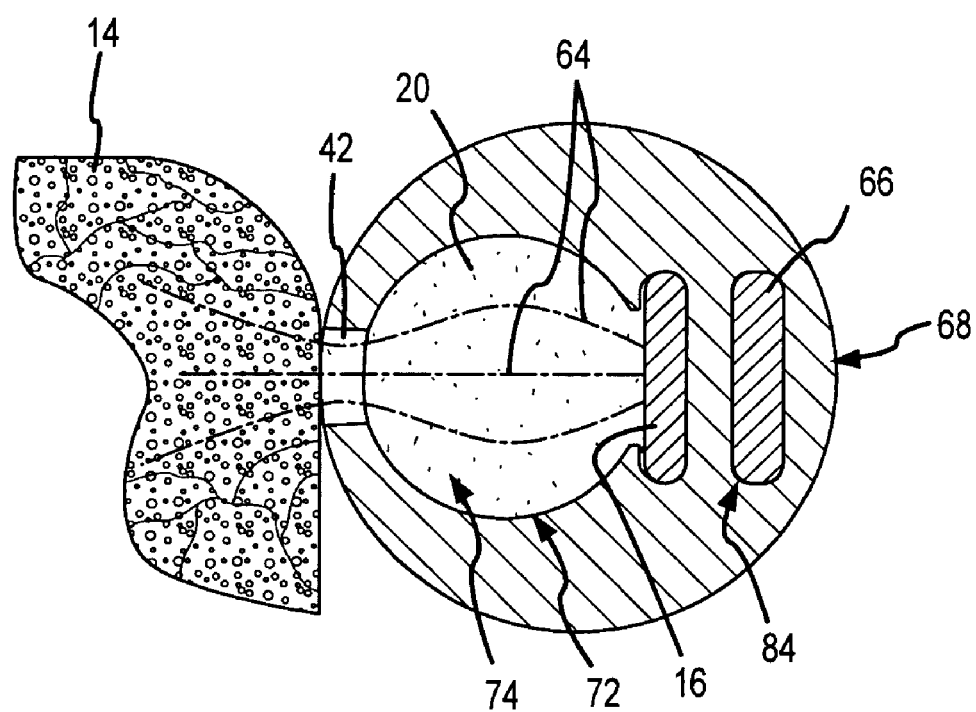
FIG. 13 is a fragmentary cross-sectional view of an ablation catheter according to the present invention and having the cross-sectional configuration depicted in FIG. 8, wherein the electrode is delivering energy to adjacent tissue.

In FIG. 12, the distal portion 12 of the ablation catheter 18 has been inserted into the left superior pulmonary vein 50. While the ablation catheter 18 is in the pulmonary vein as depicted in FIG. 12, the electrode would be activated to create the desired lesion in the left superior pulmonary vein 50. As shown in FIG. 13, the RF electric current 64 emanating from the metal electrode 16 passes through the conductive fluid medium 20 contained in the nearly-circular subportion 74 of the first lumen 72 through the portholes 42 and into the adjacent tissue 14. The conductive fluid medium 20 experiences ohmic heating as it flows along the metal electrode 16 and out the portholes 42. Thus, a lesion is formed in the tissue 14 by the RF energy 64. Lesion formation may also be facilitated by the conductive fluid medium 20, which may have been heated by ohmic heating to a sufficiently high temperature to facilitate or enhance lesion formation, flowing out the portholes. The RF energy is conducted into the adjacent tissue and the heated conductive fluid medium convectively affects the temperature of the tissue. In order to form a sufficient lesion, it is desirable to raise the temperature of the tissue to at least 50° C. for an appropriate length of time (e.g., one minute). Thus, sufficient RF energy must be supplied to the metal electrode to produce this lesion-forming temperature in the adjacent tissue for the desired duration.

The conductive fluid medium 20 flowing through the portholes 40-44 prevents blood from flowing into the ablation catheter 18 and pushes blood from the area adjacent to the portholes 40-44. This helps prevent coagulum, which can have undesirable effects on the patient. The conductive fluid medium is caused to flow at a rate that prevents the electrode from overheating the conductive fluid medium and producing vapor in the first lumen 72. If the conductive fluid medium were to boil, creating a vapor, the ablation catheter's ability to form a desired lesion in adjacent tissue 14 would be reduced or destroyed since the RF energy would be unable to reach the tissue in sufficient quantity. Thus, the flow of conductive fluid medium through the first lumen and out the portholes is managed or regulated so that there is sufficient flow to prevent vaporization, but not so much flow that the metal electrode is prohibited from sufficiently heating the adjacent tissue to form a desired lesion. Also, if too much conductive fluid medium flows out of the portholes, the hemodynamics of the patient may be adversely affected by the excess quantity of conductive fluid medium being mixed with the patient's blood. The desired flow rate is achieved by, for example, adjusting the pressure driving the conductive fluid medium through the first lumen, changing the diameter or distribution of the portholes, altering the spacing between the portholes, and changing the porthole diameter gradient between the small first porthole and the relatively larger last porthole. Another factor that may be taken into account when adjusting the flow rate of the conductive fluid medium is the specific configuration of the distal portion of the ablation catheter since the flow of conductive fluid medium is affected by the curvature of the catheter shaft.

Figure 2:
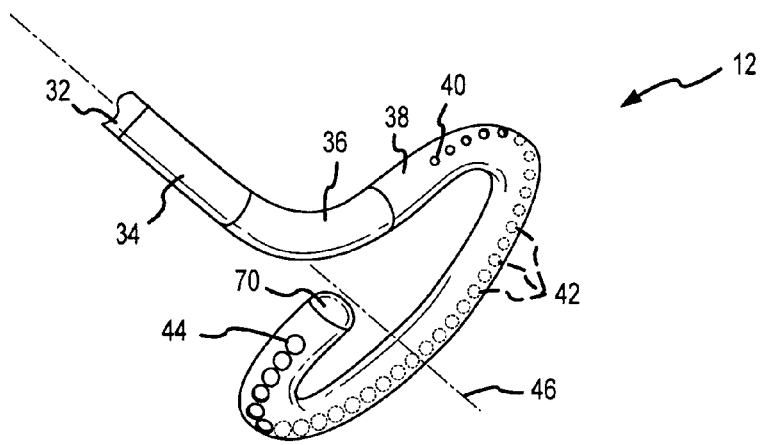
FIG. 2 is a fragmentary, isometric view of a distal portion of an ablation catheter comprising part of the ablation catheter assembly depicted in FIG. 1.
Figures 3, 4:
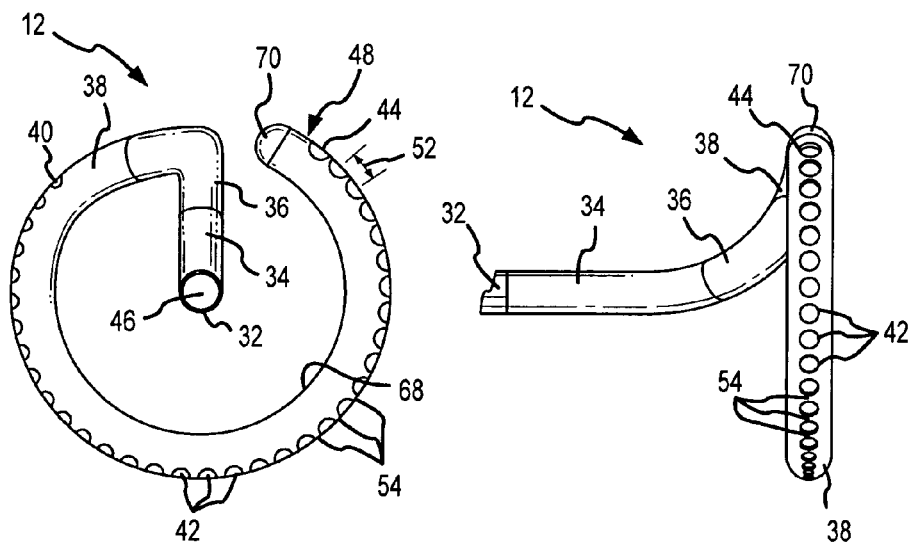
FIG. 3 is a fragmentary view along line 3-3 of FIG. 5 of the distal portion of the ablation catheter depicted in FIGS. 1 and 2 looking down the longitudinal axis of a catheter shaft comprising part of the ablation catheter.
FIG. 4 is a fragmentary view of the distal portion of the ablation catheter depicted in FIGS. 1-3, looking perpendicular to the longitudinal axis of the catheter shaft.
Figure 5:
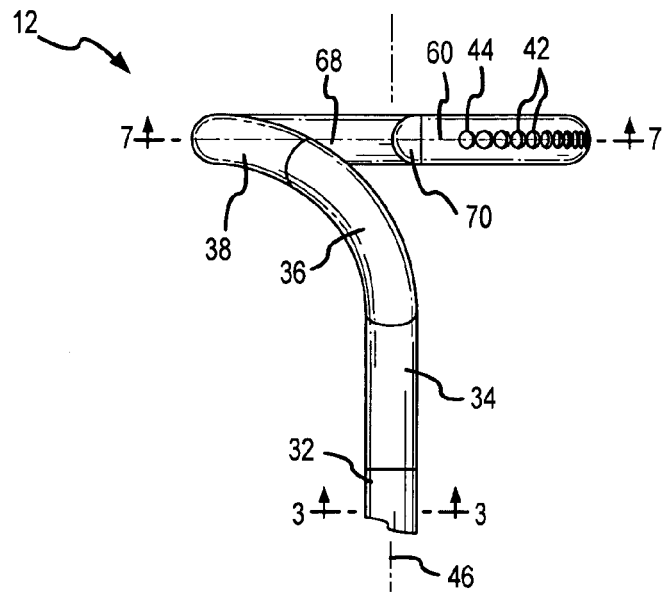
Figure 14:
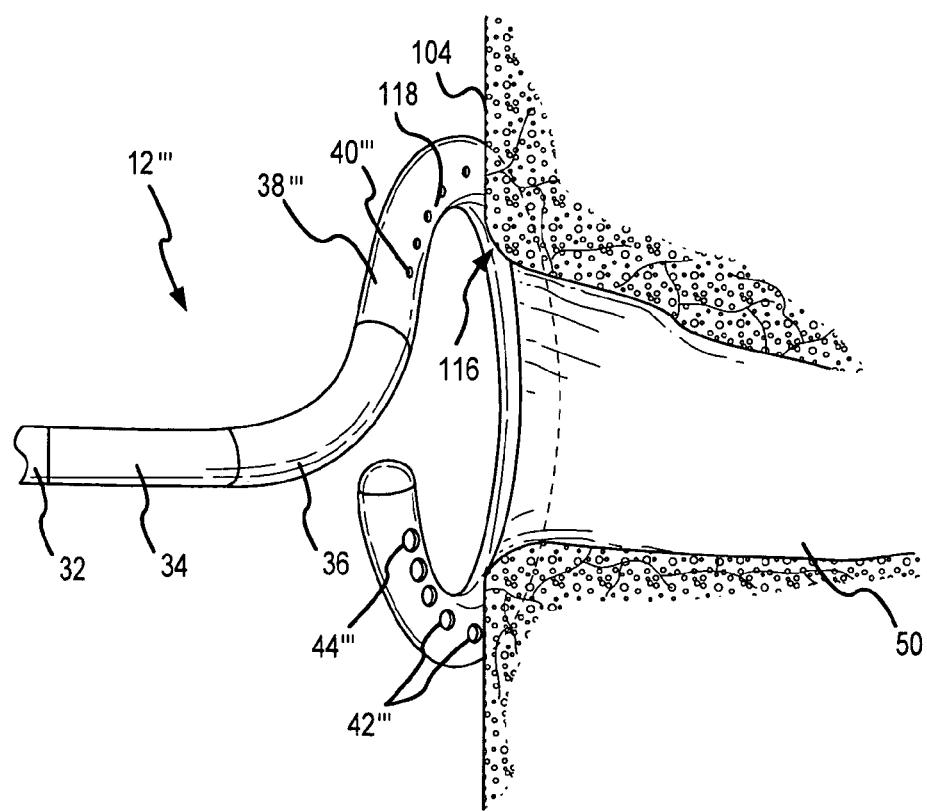
FIG. 14 depicts a third alternative configuration of an ablation catheter according to the present invention, wherein the portholes are configured to permit formation of a lesion within the left atrium at the ostium of a pulmonary vein.

In the alternative embodiment of a distal portion 12''' depicted in FIG. 14, the portholes 40-44 depicted in, for example, FIG. 2 have been moved from the longitudinally-extending tangent line 60 (FIG. 5) on the radial apex of the outer peripheral wall 48 of the third curved section 38 of catheter shaft to a distally-facing surface 118 at the distal apex of a third curved section 38'''. In this configuration, the longitudinal axes of the portholes extend parallel to the longitudinal axis 46 (see FIGS. 2, 3, and 5) of the straight section 32 of catheter shaft 22, rather than extending radially outwardly from that longitudinal axis of the straight section of catheter shaft as is the case with the embodiment of FIGS. 2-5 and 7. As with the embodiments described above, the longitudinal axis 46 of the straight section 32 of catheter shaft is substantially aligned with a longitudinal axis of a pulmonary vein (e.g., 50 in FIG. 14). When the configuration depicted in FIG. 14 is used for pulmonary vein ablation, it is unnecessary to insert the distal portion 12''' of the ablation catheter into the pulmonary vein (compare FIG. 12, wherein the distal portion 12 has been inserted into the left superior pulmonary vein 50). Rather, as shown in FIG. 14, the distal portion of the ablation catheter is placed at the ostium 116 of the pulmonary vein 50 so that the third curved section 38''' of catheter shaft substantially encircles the extended longitudinal axis (not shown) of the pulmonary vein 50. If RF energy is then applied to the ablation catheter, a circular lesion is formed in the left atrium 104 at the ostium 116 of the pulmonary vein 50, thereby inhibiting entry of stray electrical signals from the pulmonary vein 50 into the left atrium 104.

Although preferred embodiments of this invention have been described above with a certain degree of particularity, those skilled in the art could make numerous alterations to the disclosed embodiments without departing from the spirit or scope of this invention. For example, the portholes 40-44 are shown at the radial apex of the outer peripheral wall 48 of the third curved section 38 in the embodiment of FIGS. 2-5 and 7, and the portholes 40'''-42''' are shown at the distal apex of the third curved section 38''' in the embodiment of FIG. 14. The portholes could, however, pass through the outer peripheral wall of the third curved section at a location between the radial apex and the distal apex. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ablation catheter for ablating tissue, the ablation catheter comprising:
   a catheter shaft having a proximal portion and a distal portion adapted to be inserted into a body cavity having tissue to be ablated and being disposed remotely from said proximal portion,
   said distal portion comprising an active region including a plurality of substantially uniformly spaced portholes of varying cross-sectional area, wherein said portholes are adapted to deliver a conductive fluid medium to the tissue to be ablated;

a lumen extending from said proximal portion to said distal portion, said lumen being adapted to carry the conductive fluid medium from said proximal portion to said plurality of portholes along said active region of said distal portion; and a shape memory wire mounted within said lumen and extending through and shaping at least a portion of said distal portion, wherein said shape memory wire is further adapted to supply ablation energy to the conductive fluid medium within said active region.

2. The ablation catheter according to claim 1, wherein said shape memory wire has a coating of a conductive, biocompatible material.

3. An ablation catheter for ablating tissue, the ablation catheter comprising a catheter shaft comprising
a proximal portion;
a distal portion, said distal portion being adapted to be inserted into a body cavity having tissue to be ablated and being disposed remotely from said proximal portion, said distal portion comprising an active region including a plurality of portholes including a most-proximal porthole, a most-distal porthole, and an intermediate porthole therebetween, wherein said portholes are adapted to deliver a conductive fluid medium to the tissue to be ablated, wherein a relative size of said portholes changes from a first size of said most-proximal porthole to a second size of said most-distal porthole, wherein said intermediate porthole is a third size different from said first size and said second size, and wherein said portholes are circular in cross section and a relative diameter of said portholes increases in size as one moves distally from said most-proximal porthole to said most-distal porthole; and a first lumen extending from said proximal portion to said distal portion, said first lumen being adapted to carry the conductive fluid medium from said proximal portion to said plurality of portholes along said active region of said distal portion; and a metal electrode mounted within said first lumen and extending along said active region of said distal portion, wherein said metal electrode is adapted to supply ablation energy to the conductive fluid medium.

4. The ablation catheter of claim 3, wherein each of said portholes defines a proximal leading edge and a distal trailing edge, and wherein a bridge is defined between a proximal leading edge of one porthole and a distal trailing edge of a next adjacent porthole, and wherein said bridges between adjacent portholes decrease in size as one moves distally from said most-proximal porthole to said most-distal porthole.

5. The ablation catheter of claim 3, wherein said portholes are centered along a porthole centerline defined by a tangent line on a surface of said catheter shaft extending parallel to a longitudinal axis of said catheter shaft on an outer peripheral wall of said distal portion of said ablation catheter.

6. An ablation catheter for ablating tissue, the ablation catheter comprising:

a catheter shaft, said catheter shaft comprising:
a proximal portion;
a distal portion, said distal portion being adapted to be inserted into a body cavity having tissue to be ablated and being disposed remotely from said proximal portion, said distal portion comprising an active region including a plurality of portholes including a most-proximal porthole, a most-distal porthole, and an intermediate porthole therebetween, wherein said portholes are adapted to deliver a conductive fluid medium to the tissue to be ablated, wherein said portholes are of varying cross-sectional area; and a first lumen extending from said proximal portion to said distal portion, said first lumen being adapted to carry the conductive fluid medium from said proximal portion to said plurality of portholes along said active region of said distal portion; and a metal electrode mounted within said first lumen and extending along said active region of said distal portion, wherein said metal electrode is adapted to supply ablation energy to the conductive fluid medium.

7. The ablation catheter according to claim 6, wherein said portholes are substantially circular in cross section.

8. The ablation catheter according to claim 6, wherein a relative size of said portholes increases in cross-sectional area moving distally from said most-proximal porthole to said most-distal porthole.

9. The ablation catheter according to claim 6, wherein each of said portholes defines a proximal leading edge and a distal trailing edge, and wherein a bridge is defined between a proximal leading edge of one porthole and a distal trailing edge of a next adjacent porthole, and wherein said bridges between adjacent portholes decrease in size moving distally from said most-proximal porthole to said most-distal porthole.

10. The ablation catheter according to claim 6, wherein said portholes are centered along a porthole centerline defined by a tangent line on a surface of said catheter shaft extending parallel to a longitudinal axis of said catheter shaft on an outer peripheral wall of said distal portion of said ablation catheter.

11. The ablation catheter according to claim 6, wherein each of said portholes has a longitudinal centerline, and wherein distances between said longitudinal centerlines of adjacent portholes remain substantially constant along said active region.

12. The ablation catheter according to claim 6, wherein said portholes are disposed on opposing sides of a longitudinally-extending, circumferential tangent line on an outer peripheral wall of said distal portion of said ablation catheter.

13. The ablation catheter according to claim 6, wherein said metal electrode comprises shape memory wire.

14. The ablation catheter according to claim 6, wherein said metal electrode is mounted within said first lumen adjacent an inner peripheral wall of said distal portion.

* * * * *